(12) United States Patent
Pai et al.

(10) Patent No.: US 6,572,884 B1
(45) Date of Patent: Jun. 3, 2003

(54) PARENTERAL CISPLATIN EMULSION

(75) Inventors: Srikanth Annappa Pai, Thane (IN); Sangeeta Hanurmesh Rivankar, Thane (IN); Shilpa Sudhakar Kocharekar, Thane (IN)

(73) Assignee: Daftary Gautam Vinod, State of Maharashtra (IN)

( * ) Notice: Subject to any disclaimer, the term of this patent is extended or adjusted under 35 U.S.C. 154(b) by 19 days.

(21) Appl. No.: 10/048,151

(22) PCT Filed: Jul. 26, 2000

(86) PCT No.: PCT/IN00/00069

§ 371 (c)(1),
(2), (4) Date: Jun. 14, 2002

(87) PCT Pub. No.: WO01/07058

PCT Pub. Date: Feb. 1, 2001

(30) Foreign Application Priority Data

Jul. 28, 1999 (IN) ......................................... 535/BOM/99

(51) Int. Cl.$^7$ ........................... A61K 9/66; A61K 33/24; A01N 59/16

(52) U.S. Cl. ........................................ 424/455; 424/617

(58) Field of Search .................................. 424/455, 617

Primary Examiner—Alton Pryor
(74) Attorney, Agent, or Firm—Thorpe North & Western

(57) ABSTRACT

A sterile pharmaceutical cisplatin composition as an oil-in-water emulsion having low toxicity for parenteral administration comprising:

a) an oily phase selected from the group consisting of: vegetable oils, esters of medium or long chain fatty acids, and fractionated or modified oils;
   b) cisplatin incorporated in the oily phase;
   c) an emulsifier selected from the group consisting of: natural phosphatides; modified phosphatides, and synthetic non-ionic surfactants;
   d) a tonicity modifying agent selected from the group of compounds consisting of: glycerin, mannitol, and dextrose;
   e) a chelating agent selected from the group of compounds consisting of: edetates, and desferrioxamine mesylate; and
   f) water.

36 Claims, No Drawings

PARENTERAL CISPLATIN EMULSION

This application is a 371 of PCT/IN00/00069 filed Jul. 26, 2000.

FIELD OF THE INVENTION

The present invention is related to Cisplatin emulsion formulation with reduced toxicity, which is suitable for parenteral administration.

BACKGROUND OF THE INVENTION

Cisplatin-cis-diamino-dichloroplatinum (CDDP) is a heavy metal complex containing a central atom of platinum surrounded by two chlorine atoms and two ammonium molecules in cis position. It is a potent anticancer drug used in the treatment of various solid tumors particularly of testes, ovaries and bladder. Cisplatin covalently binds to DNA bases and disrupts DNA function. Cisplatin is inactivated intracellularly and in the blood stream by sulfhydryl groups. U.S. Pat. No. 4,302,446 (1981) and U.S. Pat. No. 4,322,391 (1982) patents describe preparation of cisplatin in microcrystalline form for ready solubility. U.S. Pat. No. 4,310,515 (1982) patent describes the method for preparing sterile aqueous solution of cisplatin. U.S. Pat. No. 4,915,956 (1990) patent also describes similar method for preparing sterile aqueous solution of cisplatin.

Cisplatin is highly toxic when administered as aqueous solution affecting kidneys, bone marrow and ears. Nephrotoxicity is the main dose limiting factor as 90% of cisplatin that is excreted from the body is removed from the kidney as a combination of glomerular filtration and tubular secretion (*Physician Desk Reference* $53^{rd}$ *edition:* 1999).

Various attempts have been made to reduce the nephrotoxicity of the drug. These include adequate hydration and maintenance of urinary output before and for 24 hours after administration, I.V. Infusion of Amifostine at a dose of 910 mg/m$^2$, 30 minutes prior to starting Cisplatin therapy. However these have been found inadequate.

Other attempts to minimise the nephrotoxicity of Cisplatin include combination chemotherapy, preparation of cisplatin analogues, entrapment of cisplatin in liposomes etc.

Cisplatin is difficult to entrap in liposomes efficiently because of its low aqueous solubility. Further it is difficult to stabilise the liposome preparation as it has been reported that Cisplatin is not retained in liposomal preparation during storage (Potkul, et. al. *Am. J. Obstet. Gynecol.* 164(2): 652–658; 1991. Gondal, et. al. *Eur. J. Cancer* 29A(11):1536–1542: 1993, Weiss, et. al. *Drugs* 46(3): 3660–377; 1993).

The main objective of the present invention is to develop a formulation of cisplatin that will be effective as an antineoplastic drug suitable for parenteral administration in human beings and other mammals but at the same time will not be as toxic as conventional aqueous solutions.

SUMMARY OF THE INVENTION

Accordingly, the present invention relates to a sterile pharmaceutical cisplatin composition as an oil-in-water emulsion having low toxicity for parenteral administration comprising
a) oily phase selected from group of vegetable oils, esters of medium or long chain fatty acids, fractionated or modified oil;
b) cisplatin (incorporated in oily phase);
c) emulsifiers such as natural phosphatides, modified phosphatides, synthetic non-ionic surfactants;
d) tonicity modifying agents selected from a group of compounds such as glycerin, mannitol, dextrose;
e) chelating agents selected from a group of compounds such as as edetates, desferrioxamine mesylate; and
f) water.

The process of making the above composition comprises dispersing Cisplatin in oily phase, preparing aqueous phase with tonicity modifying agent, chelating agent; adjusting pH to 8–11 and emulsifying the two phases after addition of emulsifying agent either to the aqueous phase or to the oily phase or to both phases; homogenising the emulsion to a particle size below 2 microns, keeping temperature of homogenised product below 25° C.; filtering, filling in glass containers under nitrogen, sealing the filled containers and sterilising the sealed containers by autoclaving.

A composition of this invention comprises 0.005% to 0:5% by weight of Cisplatin, Preferably the composition comprises from 0.05 to 0.1% by weight of Cisplatin and more preferably about 0.05% or about 0.1% by weight of Cisplatin.

Cisplatin is dispersed in a oily phase prior to emulsification. Oily phase is present in an amount that is up to 30% by weight of the composition, preferably 5 to 25% and more preferably about 10% or about 20%. Typically the oily phase used is a vegetable oil and can be one or more of the vegetable oils such as soybean oil, sesame oil, cotton seed oil, safflower oil, sunflower oil, arachis oil, corn oil, castor oil or olive oil. Preferably the vegetable oil is soybean oil.

Alternatively the oily phase is an ester of medium or long chain fatty acids such as mono, di, or triglyceride or prepared material such as isopropyl myristate, isopropyl palmitate, ethyl oleate, a glycerol ester or polyoxyl hydrogenated castor oil. Oily phase can also include fractionated oil such as fractionated coconut oil or modified soybean oil. The composition of the present invention can also comprise a mixture of two or more of the above mentioned oily vehicles.

Cisplatin dispersed in an oily phase, is emulsified by means of emulsifier to give oil-in-water emulsion. Suitable emulsifiers include naturally occurring phosphatides and modified phosphatides. Naturally occurring phosphatides include egg phosphatide and soya phosphatides. Alternatively the emulsifier can be synthetic non-ionic surfactants such as ethoxylated ethers and esters and polyoxyethylene-polyoxypropylene co-polymers. Emulsifier used in the present invention may comprise a mixture of two or more of the above mentioned emulsifiers. Preferred emulsifiers arc egg and soya phosphatides.

The composition of the present invention is formulated suitably to exclude heavy metal contamination by using chelating agents. The chelating agents are selected from ethylenediaminetetraacetic acid (EDTA), derivatives of EDTA and desferrioxamine mesylate or a mixture thereof. Specifically the chelating agent used is disodium edeta.

The composition of the present invention is formulated suitably for the pH range to be at 6.0–8.5. pH is adjusted with an alkali such as sodium hydroxide or potassium hydroxide or a mixture thereof.

The composition of the present invention is made isotonic with blood by incorporation of a tonicity modifying agent such as glycerin, mannitol, dextrose, or a mixture thereof. Preferred tonicity modifying agent is glycerin.

The compositions of the present invention are specifically sterile oil-in-water emulsions and are prepared according to the conventional manufacturing procedures using aseptic techniques or terminal sterilisation by autoclaving.

In main embodiment of the invention, Cisplatin is dispersed in oily phase.

In another embodiment of the invention the type of emulsion prepared is oil-in-water type and Cisplatin is in oily phase.

In another embodiment of the invention, chelating agents are used in the emulsions to stabilise the emulsion, and prevent its discolouration.

In another embodiment of the invention, the homogenisation is done in repeated cycles to achieve less than 2 microns particle/globule size with intermediate cooling of the homogenised product to a temperature less than about 25° C.

The composition of the present invention gives a product with reduced toxicity which is also suitable for parenteral use because of low particle size. Sterility, of the composition of the present invention is assured because the product is sterilised by end autoclaving. The composition of the present invention is easy to use as the product could be diluted with dextrose injection 5% or saline to get the required concentration for parenteral administration. The composition of the present invention also has a prolonged shelf life and hence suitable for a ready marketable product.

EXAMPLES

The invention will now be illustrated by way of examples. The examples are by way of illustration only and in no way restrict the scope of the invention.

All the raw materials used in these examples were of parenteral grade. Equipments used were of conventional nature. Entire processing was done in an area with a controlled environment. Nitrogen cover was provided while processing the batch.

Example I

Composition:
a) Cisplatin 0.05% by weight
b) Soybean oil 10% by weight
c) Egg phosphatide 1.2% by weight
d) Glycerin 2.25% by weight
e) Disodium edetate 0.005% by weight
f) Sodium hydroxide
g) Water up to 100%

Oil phase—Cisplatin was dispersed in filtered soybean oil previously maintained at about 70° C.

Aqueous phase—Glycerin and disodium EDTA were added to Water for Injection maintained at about 70° C. Egg phosphatide was dispersed in this aqueous solution and pH was adjusted to 8–11 using aqueous sodium hydroxide solution.

Oily phase prepared above was added to the aqueous phase under high speed stirring. The emulsion formed was passed through the high pressure homogeniser.

Homogenisation was repeated till the globule/particle size was below 2 microns. The product was cooled to below 25° C. immediately after each homogenisation cycle.

The homogenised emulsion was filtered and filled into glass containers under nitrogen, sealed and autoclaved. The final product of this example had cisplatin content 0.5 mg/ml.

Example II

The composition prepared in this example had same ingredients as in Example I except for some changes in quantities of certain ingredients as shown below:

ii) Cisplatin 0.1% by weight
iii) Soybean oil 20% by weight
iii) Disodium EDTA 0.05% by weight Processing was done as per Example I.

The final product of this example had cisplatin content 1 mg/m.

The oil-in-water emulsion of Cisplatin prepared as per Example I was used for toxicity studies in mice.

Toxicity Study in Mice

The toxicity of Cisplatin oil-in-water emulsion prepared by the process described under Example I and that of cisplatin aqueous solution prepared by the conventional process was studied in mice.

a) Following, tests were carried out and the observations are presented in the following Table

| PARAMETER | CISPLATIN O/W EMULSION OF EXAMPLE I (22 mg/kg)* | CISPLATIN AQUEOUS SOLUTION (CONVENTIONAL) (22 mg/kg)* |
|---|---|---|
| BUN | 13 mg/dl | 99.9 mg/dl |
| BLOOD UREA | 28 mg/dl | 214 mg/dl |
| CREATININE | 0.5 mg/dl | 1.9 mg/dl |
| SGOT | 200 units | 605 units |
| SGPT | 78 units | 109 units |

*Dosage of cisplatin b) Histopathological Studies

Histopathological studies in mice indicated more severe lesions in kidneys in Cisplatin aqueous solution group than Cisplatin emulsion group when studied in equivalent doses.

c) Subacute Toxicity Studies

In subacute toxicity studies in mice, Cisplatin emulsion and Cisplatin aqueous solution were administered intraperitoncally over a period of 14 days. The following were the findings.

Mice injected with Cisplatin aqueous solution showed 62.5% mortality at 2 mg/kg and 100% mortality at doses of 4 mg/kg and above.

Mice injected with Cisplatin emulsion showed only 37.5% mortality at 10 mg/kg dose.

| $LD_{50}$ (Intraperitonial) | |
|---|---|
| Cisplatin aqueous solution | 22 mg/kg |
| Cisplatin o/w emulsion | 50 mg/kg |

When tested at dose levels ranging from 2 mg/kg to 10 mg/kg of cisplatin for various parameters like organ weight, body weight, food consumption, hematological parameters; Cisplatin emulsion of Example I showed toxicity only at the highest dose of 10 mg/kg whereas Cisplatin aqueous solution showed toxicity at all doses from 2 to 10 mg/kg. This study reveals that Cisplatin emulsion prepared by process of Example I is relatively much less toxic than conventional Cisplatin aqueous solution.

This study clearly shows that the emulsion prepared by the process of invention is a synergistic composition.

What is claimed is:

1. A sterile pharmaceutical cisplatin composition as an oil-in-water emulsion having low toxicity for parenteral administration comprising:

a) an oily phase selected from the group consisting of: vegetable oils, esters of medium or long chain fatty acids, and fractionated or modified oils;

b) cisplatin incorporated in the oily phase;
c) an emulsifier selected from the group consisting of: natural phosphatides; modified phosphatides, and synthetic non-ionic surfactants;
d) a tonicity modifying agent selected from the group of compounds consisting of: glycerin, mannitol, and dextrose;
e) a chelating agent selected from the group of compounds consisting of: edetates, and desferrioxamine mesylate; and
f) water.

2. A sterile pharmaceutical cisplatin composition as an oil-in-water emulsion having low toxicity for parenteral administration as claimed in claim 1 wherein the content of Cisplatin is from 0.005% to 0.5% by weight of the composition.

3. A sterile pharmaceutical cisplatin composition as an oil-in water emulsion having low toxicity for parenteral administration as claimed in claim 1 wherein the content of Cisplatin is from 0.05% to 0.1% by weight of the composition.

4. A sterile pharmaceutical cisplatin composition as an oil-in-water emulsion having low toxicity for parenteral administration as claimed in claim 1 wherein the content of Cisplatin is about 0.05% by weight of the composition.

5. A sterile pharmaceutical cisplatin composition as an oil-in-water emulsion having low toxicity for parenteral administration as claimed in claim 1 wherein the content of Cisplatin is about 0.1% by weight of the composition.

6. A sterile pharmaceutical cisplatin composition as an oil-in-water emulsion having low toxicity for parenteral administration as claimed in claim 1 wherein the oily phase is up to 30% by weight of the composition.

7. A sterile pharmaceutical cisplatin composition as an oil-in-water emulsion having low toxicity for parenteral administration as claimed in claim 1 wherein the oily phase is from about 10% to 20% by weight of the composition.

8. A sterile pharmaceutical cisplatin composition as an oil-in-water emulsion having low toxicity for parenteral administration as claimed in claim 1 wherein the oily phase is vegetable oil or fractionated vegetable oil or modified vegetable oil or ester of a fatty acid or a mixture thereof.

9. A sterile pharmaceutical cisplatin composition as an oil-in-water emulsion having low toxicity for parenteral administration as claimed in claim 1 wherein the vegetable oil is soybean oil.

10. A sterile pharmaceutical cisplatin composition as an oil-in-water emulsion having low toxicity for parenteral administration as claimed in claim 1 wherein the chelating agent used is disodium edetate.

11. A sterile pharmaceutical cisplatin composition as an oil-in-water emulsion having low toxicity for parenteral administration as claimed in claim 1 wherein the content of disodium edetate is up to about 0.1% by weight of the composition.

12. A sterile pharmaceutical cisplatin composition as an oil-in-water emulsion having low toxicity for parenteral administration as claimed in claim 1 wherein the content of disodium edetate is from about 0.005% to 0.05% by weight of the composition.

13. A sterile pharmaceutical cisplatin composition as an oil-in-water emulsion having low toxicity for parenteral administration as claimed in claim 1 wherein the emulsifier used is a natural phosphatide.

14. A sterile pharmaceutical cisplatin composition as an oil-in-water emulsion having low toxicity for parenteral administration as claimed in claim 1 wherein the natural phosphatide is egg phosphatide or soya phosphatide or a mixture thereof.

15. A sterile pharmaceutical cisplatin composition as an oil-in-water emulsion having low toxicity for parenteral administration as claimed in claim 1 wherein said tonicity said modifier used is in a quantity sufficient to make the product isotonic with blood.

16. A sterile pharmaceutical cisplatin composition as an oil-in-water emulsion having low toxicity for parenteral administration as claimed in claim 1 wherein said tonicity modifier used is glycerin.

17. A sterile pharmaceutical cisplatin composition as an oil-in-water emulsion having low toxicity for parenteral administration as claimed in claim 1 wherein the content of glycerin is about 2.25% by weight of the composition.

18. A sterile pharmaceutical cisplatin composition as an oil-in-water emulsion having low toxicity for parenteral administration as claimed in claim 1 wherein aqueous sodium hydroxide is used to get required pH.

19. A process for the preparation of a sterile pharmaceutical cisplatin composition as an oil-in-water emulsion having low toxicity for parenteral administration as claimed in claim 1 comprising dispersing Cisplatin in oily phase, preparing aqueous phase with said tonicity modifying agent, said chelating agent; adjusting pH to 8–11 and emulsifying the two phases after addition of said emulsifying agent either to the aqueous phase or to the oily phase or to both phases; homogenizing the emulsion to a particle size below 2 microns, keeping temperature of homogenized product below about 25° C.; filtering, filling in glass containers under nitrogen, sealing the filled containers and sterilizing the sealed containers by autoclaving.

20. A process for the preparation of a sterile pharmaceutical cisplatin composition as an oil-in-water emulsion having low toxicity for parenteral administration as claimed in claim 19 wherein the content of Cisplatin is from 0.005% to 0.5% by weight of the composition.

21. A process for the preparation of a sterile pharmaceutical cisplatin composition as an oil-in-water emulsion having low toxicity for parenteral administration as claimed in claim 19 wherein the content of Cisplatin is from 0.05% to 0. 1% by weight of the composition.

22. A process for the preparation of a sterile pharmaceutical cisplatin composition as an oil-in-water emulsion having low toxicity for parenteral administration as claimed in claim 19 wherein the content of Cisplatin is about 0.05% by weight of the composition.

23. A process for the preparation of a sterile pharmaceutical cisplatin composition as an oil-in-water emulsion having low toxicity for parenteral administration as claimed in claim 19 wherein the content of Cisplatin is about 0.1% by weight of the composition.

24. A process for the preparation of a sterile pharmaceutical cisplatin composition as an oil-in-water emulsion having low toxicity for parenteral administration as claimed in claim 19 wherein the oily phase is up to 30% by weight of the composition.

25. A process for the preparation of a sterile pharmaceutical cisplatin composition as an oil-in-water emulsion having low toxicity for parenteral administration as claimed in claim 19 wherein the oily phase is from about 10% to 20% by weight of the composition.

26. A process for the preparation of a sterile pharmaceutical cisplatin composition as an oil-in-water emulsion having low toxicity for parenteral administration as claimed in claim 19 wherein the oily phase is vegetable oil or fractionated vegetable oil or modified vegetable oil or ester of a fatty acid or a mixture thereof.

27. A process for the preparation of a sterile pharmaceutical cisplatin composition as an oil-in-water emulsion having low toxicity for parenteral administration as claimed in claim 19 wherein the vegetable oil is soybean oil.

28. A process for the preparation of a sterile pharmaceutical cisplatin composition as an oil-in-water emulsion having low toxicity for parenteral administration as claimed in claim 19 wherein the chelating agent used is disodium edetate.

29. A process for the preparation of a sterile pharmaceutical cisplatin composition as an oil-in-water emulsion having low toxicity for parenteral administration as claimed in claim 19 wherein content of disodium edetate is up to about 0.1% by weight of the composition.

30. A process for the preparation of a sterile pharmaceutical cisplatin composition as an oil-in-water emulsion having low toxicity for parenteral administration as claimed in claim 19 wherein content of disodium edetate is from about 0.005% to 0.05% by weight of the composition.

31. A process for the preparation of a sterile pharmaceutical cisplatin composition as an oil-in-water emulsion having low toxicity for parenteral administration as claimed in claim 19 wherein the emulsifier used is said natural phosphatide.

32. A process for the preparation of a sterile pharmaceutical cisplatin composition as an oil-in-water emulsion having low toxicity for parenteral administration as claimed in claim 19 wherein the natural phosphatide is egg phosphatide or soya phosphatide or a mixture thereof.

33. A process for the preparation of a sterile pharmaceutical cisplatin composition as an oil-in-water emulsion having low toxicity for parenteral administration as claimed in claim 19 wherein the tonicity modifier used is in a quantity sufficient to make the product isotonic with blood.

34. A process for the preparation of a sterile pharmaceutical cisplatin composition as an oil-in-water emulsion having low toxicity for parenteral administration as claimed in claim 19 wherein the tonicity modifier used is glycerin.

35. A process for the preparation of a sterile pharmaceutical cisplatin composition as an oil-in-water emulsion having low toxicity for parenteral administration as claimed in claim 19 wherein the content of glycerin is about 2.25% by weight of the composition.

36. A process for the preparation of a sterile pharmaceutical cisplatin composition as an oil-in-water emulsion having low toxicity for parenteral administration as claimed in claim 19 wherein aqueous sodium hydroxide is used to get the required pH.

\* \* \* \* \*